United States Patent [19]

Lobdell et al.

[11] 4,237,091
[45] Dec. 2, 1980

[54] TEMPERATURE PROBE

[75] Inventors: Donn D. Lobdell, Golden; Stephen J. Herman, Evergreen; Robert L. Anderson, Boulder, all of Colo.

[73] Assignee: Cobe Laboratories, Inc., Lakewood, Colo.

[21] Appl. No.: 917,469

[22] Filed: Jun. 21, 1978

[51] Int. Cl.³ .............................................. A61M 1/03
[52] U.S. Cl. ...................................... 422/46; 165/11R; 403/349; 73/343 B; 73/362.8; 73/375; 422/47
[58] Field of Search .............. 73/339 R, 343 B, 362.8, 73/374, 375; 422/45, 46, 47; 403/348, 349, 361; 206/305, 306, 459; 165/11

[56] References Cited

U.S. PATENT DOCUMENTS

| 899,313 | 9/1908 | Maurer | 73/374 |
| 2,135,078 | 11/1938 | Hubbard et al. | 73/339 R |
| 2,161,432 | 6/1939 | Rees | 136/4 |
| 2,981,106 | 4/1961 | Knudsen et al. | 73/339 R |
| 3,081,631 | 3/1963 | Switzer et al. | 73/343 |
| 3,321,068 | 5/1967 | Beach | 206/306 |
| 3,703,892 | 12/1970 | Meyers | 128/2 H |
| 3,833,115 | 9/1974 | Schapker | 128/2 H X |
| 3,913,402 | 10/1975 | Doyle | 73/343 R |

FOREIGN PATENT DOCUMENTS 1184837 2/1959 France ................................ 73/339 R

*Primary Examiner*—Albert W. Davis
*Assistant Examiner*—Margaret A. Focarino

[57] ABSTRACT

Making temperature measurements of blood inside a disposable, sterilized medical device by providing receptacles in the walls of the device for receiving temperature-sensitive probes, the receptacles including a tubular heat-conductive member, extending through a wall of the device and being sealed to the wall, and a cylindrical body having protuberances extending radially for cooperating with slots in a temperature-sensitive probe.

1 Claim, 4 Drawing Figures

U.S. Patent    Dec. 2, 1980    4,237,091
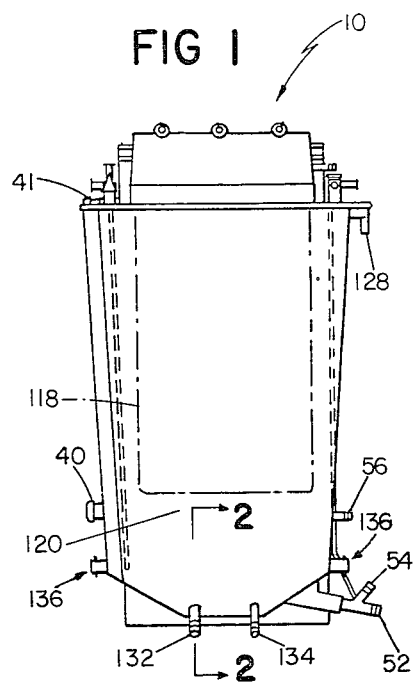
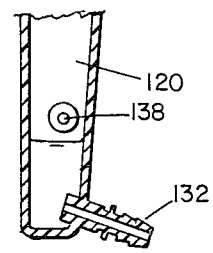
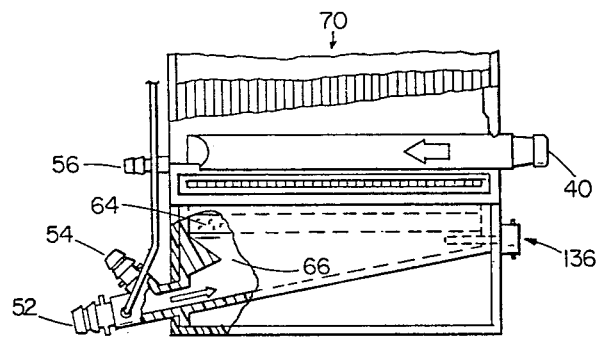
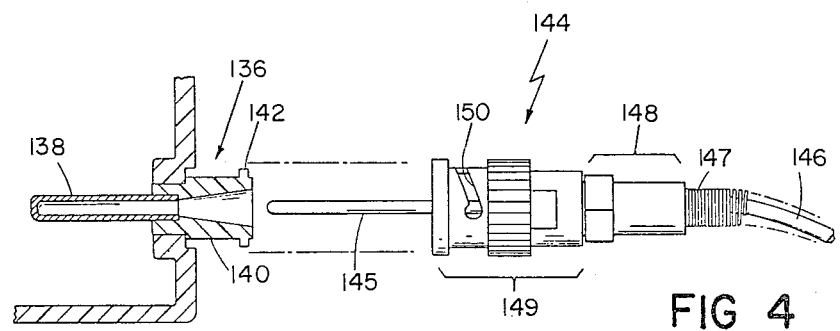

TEMPERATURE PROBE

FIELD OF THE INVENTION

This invention relates to temperature probes, particularly probes for making measurements within sterilized fluid reservoirs.

BACKGROUND OF THE INVENTION

Whenever blood is treated outside the body, such as in an oxygenator or heat exchanger, it is often desirable to measure blood temperature. Conventionally this has been done external to the oxygenator or other device by breaking a blood line to connect into the line a sterilized coupling having a temperature probe inserted through a wall. When a heat exchanger is used, two sterilized couplings are sometimes required.

Maurer U.S. Pat. No. 899,313 shows a thermometer well with a hollow body that is mounted in the wall of a vat and that has external threads outside the vat for inwardly forcing a thermometer tube so as to make firm, heat-conducting contact between the thermometer tube and the interior walls of the well.

Rees U.S. Pat. No. 2,161,432 shows a thermometer well with a corrosion resistant tube sealed at one end and threadedly received in a plug at the other, the plug having external threads for mounting in a reservoir and internal threads for securing a thermometer.

Switzer U.S. Pat. No. 3,081,631 shows a thermometer well broadly similar to Maurer and Rees for use in pipes.

Meyers U.S. Pat. No. 3,703,892; Schapker U.S. Pat. No. 3,833,115; and Doyle U.S. Pat. No. 3,913,402 each show rubber-like sheaths for clinical thermometers.

SUMMARY OF THE INVENTION

We have discovered that temperature measurements can be made of blood inside a disposable, sterilized medical device by providing receptacles in the walls of the device for receiving temperature-sensitive probes, the receptacles including a tubular heat-conductive member with one sealed end and one open end, the sealed end extending through a wall of the device and being sealed to a cylindrical body which is sealed to the wall, the cylindrical body either having protuberances extending radially for cooperating with slots in a cylindrical member supporting the temperature-sensitive probe or having slots for cooperating with protuberances in the cylindrical member supporting the temperature-sensitive probe. In preferred embodiments, the slots are helical, there are two protuberances spaced 180° apart, and the tubular member is made of stainless steel. The receptacles allow fast and reliable connection of unsterilized probes to factory-sterilized medical devices.

PREFERRED EMBODIMENT

The structure and operation of the preferred embodiment of the invention are as follows.

STRUCTURE

The drawings show the preferred embodiment and related apparatus, which are then described.

DRAWINGS

FIG. 1 is an elevation view of a blood oxygenator with which the temperature probe and receptacle is used;

FIG. 2 is a sectional view taken through 2—2 of FIG. 1, showing the lower portion of a blood reservoir with a temperature probe receptacle;

FIG. 3 is a fragmentary elevation view partially cut away, of the lower back of the blood oxygenator, showing another temperature probe receptacle; and FIG. 4 is an elevation view of the temperature probe and a sectional view of the receptacle.

DESCRIPTION

Turning to FIG. 1, there is shown blood oxygenator 10 constructed of clear polycarbonate plastic (such as Lexan, a General Electric trademark) with individual pieces adhered by solvent bonding or by a polyurethane adhesive. Blood enters the oxygenator through fittings 52, 54 which lead into chamber 66 (FIG. 3). Oxygen enters through fitting 56. Blood foam travels upward through gas and heat exchange column 70 (FIG. 3) and down through defoamer 118. Liquid blood collects in reservoir 120 and is withdrawn from the oxygenator through fittings 132, 134. Gas is exhausted through fitting 128. Temperature controlled water is circulated through column 70, entering at inlet 40 and exiting at outlet 41. Further details regarding the construction and operation of the oxygenator may be found in the copending U.S. patent application of Donn D. Lobdell and Stephen J. Herman entitled "Gas Exchange Apparatus", the contents of which are hereby incorporated by reference herein.

Temperature probe receptacles 136, are located in side walls of reservoir 120 and chamber 66 (FIGS. 1, 2, and 3). Each receptacle consists of a hollow stainless steel tube 138 (FIG. 4), which extends inside reservoir 120 and chamber 66 and is supported by a molded plastic plug 140 adhesively mounted in the basin and chamber walls and having the external shape of a BNC connector with 180°-spaced protuberances 142. Tubes 138 are closed at their furthest inward ends and open toward the outside at the ends supported in plugs 140. Each temperature-sensitive probe 144 includes a metal probe tip 145, electrical cable 146, and spring sleeve 147 (supplied as a unit under the designation Series 400 by Yellow Springs Instruments, Inc., Yellow Springs, Ohio). The Yellow Springs unit is modified by addition of a nut 148 to which is threaded on a metal BNC connector 149 (Amphenol No. 74868 UG-88/U); the central hole of the BNC is enlarged to receive probe tip 145, and the inner Teflon ring and staked metal ring (not shown) in the BNC are machined down 13/32 inch from the edge of the BNC closest to the probe tip.

OPERATION

To begin oxygenation, venous blood from a catheter or other source is supplied to the oxygenator (at a rate of approximately 5 liters per minute) by a tube (not shown) connected to barbed fitting 52. Oxygenated blood is drawn out of the oxygenator through tubes (not shown) connected to barbed fittings 132, 134. A tube connected to fitting 132 supplies blood to the arteries; another connected to fitting 134 supplies blood for direct coronary perfusion. The oxygenator is normally located below the patient, giving a static head to entering blood (patient normally at 40 inches above floor;

venous inlet fitting 52 at between 2 and 20 inches above floor).

Oxygen (or a mixture of oxygen and small percentages of either carbon dioxide and/or anesthesia) is supplied under 2 to 5 psi pressure through a tube (not shown) connected to barbed fitting 56. Exhaust gases—unused oxygen and released carbon dioxide—are drawn off under vacuum through a tube (not shown) connected to tapered fitting 128. Drawing the exhaust gases off in a tube is advantageous in preventing contamination of the operating room atmosphere with anesthesia gases introduced in the gas supplied to the oxygenator.

Gas diffuses through the many tiny holes in plug 64 and creates bubbles in the blood passing by the plug. The blood foam rises from chamber 66 into gas and heat exchange column 70. Simultaneously with gas exchange taking place in column 70 heat is exchanged between the foamed blood and the circulated water. Water enters at fitting 40 and travels upward in column 70 until exiting at outlet fitting 41. Initially entrapped air leaves with the water through fitting 41. Blood leaving column 70 is defoamed in defoamer 118 and collects in reservoir 120. Gas emerging from the burst bubbles escapes through the defoamer and is exhausted through fitting 128.

Temperature probe receptacles 136 provide points to monitor blood temperature before and after the heat exchange. Each probe tip 145 is inserted through plug 140 into tube 138, so that the end of tip 145 contacts the closed end of tube 138 and is held tightly thereagainst by means of helical slots 150 on the BNC connector receiving protuberances 142 on each plug. Cable 146 connects the probe tip to instrumentation electronics (not shown). BNC connector 149 is spring-biased to assure a tight fit between the end of tip 145 and the closed end of tube 138, thereby providing good heat transfer characteristics between the blood and probe tip.

OTHER EMBODIMENTS

The position of protuberances 142 on plug 140 and slots 150 on connector 149 could be reversed, protuberances 142 being replaced by slots similar to slots 150 and slots 150 being replaced by protuberances similar to protuberances 142.

OTHER INVENTIONS

Subject matter disclosed herein relating to the heat exchanger was the joint invention of Joel F. Giurtino and Robert I. Anderson.

INCORPORATION BY REFERENCE

We incorporate by reference the copending U.S. patent application of Donn D. Lobdell and Stephen J. Herman entitled "Gas Exchange Apparatus".

What is claimed is:
1. A disposable blood oxygenator, comprising:
   a venous blood inlet chamber comprised of a first plastic housing and a venous blood inlet connected thereto,
   bubble generating means for forming oxygen bubbles in the blood in said blood inlet chamber,
   a gas exchange column means extending upwardly above said blood inlet chamber for transporting said bubbles while gas is exchanged with the blood,
   heat exchange means downstream of said inlet chamber for exchanging heat between the blood and another fluid,
   defoaming means connected to and communicating with the outlet of said gas exchange means for breaking up bubbles,
   a blood reservoir chamber connected to and below said defoaming means for collecting oxygenated and heated blood, said reservoir chamber comprising a plastic housing, and
   blood temperature measuring means for monitoring the temperature of the blood in said inlet or reservoir chambers, each said means comprising,
      a tubular metallic heat-conductive member with one sealed end and one open end, said sealed end extending through a wall of said chamber, and the interior of said tubular member being adapted to receive an elongated temperature probe, said probe, being supported by a cylindrical member, and
      a molded plastic plug for supporting said tubular metallic member, said plug extending through and sealed to the plastic chamber wall, said tubular metallic member extending through and sealed to said plug, and said plug having means for retaining said probe in said heat-conductive member, said retaining means cooperating with said cylindrical member of said probe such that protuberances extending from said plug or said cylindrical member cooperate with helical slots on the other member,
   whereby blood temperature can be measured before or after its passage through said heat and gas exchange means by temperature probes that can be quickly twisted into sterile, secure, heat-sensing communication with the blood and quickly disengaged when the oxygenator has been used and is ready for disposal.

* * * * *